US008685057B2

(12) United States Patent  (10) Patent No.: US 8,685,057 B2
Wu  (45) Date of Patent: Apr. 1, 2014

(54) DISPOSABLE DENTAL TWEEZERS

(76) Inventor: Ming-Yuan Wu, Taipei (TW)

(*) Notice: Subject to any disclaimer, the term of this patent is extended or adjusted under 35 U.S.C. 154(b) by 162 days.

(21) Appl. No.: 13/480,740

(22) Filed: May 25, 2012

(65) Prior Publication Data

US 2013/0316301 A1  Nov. 28, 2013

(51) Int. Cl.
*A61B 17/50* (2006.01)
(52) U.S. Cl.
USPC .................................................. 606/210
(58) Field of Classification Search
USPC ............ 433/3, 141, 157, 162; 606/43, 51, 52, 606/131, 133, 205, 206, 207, 208, 210, 606/211; D24/143, 152, 153; D28/55
See application file for complete search history.

(56) References Cited

U.S. PATENT DOCUMENTS

| | | | | |
|---|---|---|---|---|
| 3,648,702 A * | 3/1972 | Bean | ................................ | 606/210 |
| 3,653,389 A * | 4/1972 | Shannon | ........................ | 606/210 |
| 3,815,607 A * | 6/1974 | Chester | .......................... | 606/210 |
| 3,815,609 A * | 6/1974 | Chester | .......................... | 606/210 |
| 3,901,243 A * | 8/1975 | Read | ................................. | 606/188 |
| 4,212,305 A * | 7/1980 | Lahay | ............................. | 606/210 |
| 4,274,413 A * | 6/1981 | Hahn et al. | ....................... | 606/42 |
| D262,055 S * | 11/1981 | Luikart, II | ..................... | D24/143 |
| 4,424,811 A * | 1/1984 | Groot | ............................... | 606/157 |
| 4,462,404 A * | 7/1984 | Schwarz et al. | .............. | 606/206 |
| 4,478,221 A * | 10/1984 | Heiss | ............................... | 606/145 |
| 4,593,693 A * | 6/1986 | Schenck | ......................... | 606/155 |
| 4,724,838 A * | 2/1988 | Hasson | .......................... | 606/148 |
| 5,002,323 A * | 3/1991 | Idsund | ........................... | 294/100 |
| 5,221,280 A * | 6/1993 | Gross et al. | ..................... | 606/36 |
| D340,173 S * | 10/1993 | Feng | ................................. | D8/52 |
| 5,250,046 A * | 10/1993 | Lee | .................................. | 606/29 |
| 5,250,075 A * | 10/1993 | Badie | ............................. | 606/207 |
| 5,334,215 A * | 8/1994 | Chen | .............................. | 606/210 |
| 6,048,341 A * | 4/2000 | Hirakawa et al. | ............... | 606/51 |
| D447,239 S * | 8/2001 | Enoch et al. | .................. | D24/153 |
| 6,471,515 B2* | 10/2002 | Feuer | ............................. | 433/162 |
| D561,942 S * | 2/2008 | Khubani | ........................ | D28/55 |
| D607,101 S * | 12/2009 | Andre | ............................ | D24/143 |
| D672,039 S * | 12/2012 | Oboh et al. | .................... | D24/143 |
| 2002/0094507 A1* | 7/2002 | Feuer | ............................. | 433/162 |
| 2002/0143363 A1* | 10/2002 | Attinger et al. | ............... | 606/210 |
| 2006/0052819 A1* | 3/2006 | Lin | ................................. | 606/211 |
| 2008/0243180 A1* | 10/2008 | Lin | ................................. | 606/211 |

* cited by examiner

*Primary Examiner* — Ryan Severson
*Assistant Examiner* — Jonathan W Miles
(74) *Attorney, Agent, or Firm* — Muncy, Geissler, Olds & Lowe, P.C.

(57) ABSTRACT

A dental tweezers with plastic tweezers main body is disclosed. A weight cavity is disposed on both tweezers arms of the main body. Weight arms of a metal weight are inserted into the weight cavities. A weight seat holds the metal weight in place on the tweezers main body. The metal weight makes the dental tweezers feel heavier and more substantial. After the dental tweezers have been used the metal weight is removed from the main body. The plastic tweezers main body is disposed of and the metal weight is retained for future use in an new plastic tweezers main body. A use indicator of the tweezers main body indicates that the dental tweezers has been used. The use indicator provides easy determination of whether or not the dental tweezers has been previously used.

20 Claims, 8 Drawing Sheets

DISPOSABLE DENTAL TWEEZERS

BACKGROUND OF THE INVENTION

1. Field of the Invention

The present invention relates to dental equipment. More specifically, the present invention discloses a weighted hand-held dental tweezers that are disposable after use in order to prevent cross-contamination between patients and eliminate the need for sterilization procedures.

2. Description of the Prior Art

Dental professionals utilize a variety of hand-held tools to perform procedures to maintain a patient's teeth and to correct dental problems.

The conventional dental tool includes a solid metal body with a metal implement on one end of the solid metal body.

Since the conventional dental tool is made completely of metal, the dental tool has a relative weight. This weight provides a balance and makes the tool comfortable to use.

However, after each use the dental tool must be sterilized before the dental tool is used with another patient in order to prevent contamination and possible infection or bacteria from being spread between patients. For example, if patient A has a virus and the dental tool used with patient A is not sterilized before using the dental tool with patient B, it is possible for patient B to contract the virus. As a result, use of the conventional dental tool has a potential risk of negatively affecting a patient's health.

Additionally, since the conventional dental tool is made of solid metal, the dental tool is relatively expensive to produce and purchase. Also, there is an associated cost involved with the sterilization procedure, sterilization equipment, and dental professional's time to perform the sterilization procedure.

Therefore, there is need for improved hand-held dental tweezers that are disposable after use thus eliminating the need for a sterilization procedure.

SUMMARY OF THE INVENTION

To achieve these and other advantages and in order to overcome the disadvantages of the conventional methods in accordance with the purpose of the invention as embodied and broadly described herein, the present invention provides a hand-held dental tweezers that is relatively inexpensive and is disposable after use in order to eliminate sterilization procedures and prevent contamination from being pass between patients.

The disposable dental tweezers of the present invention comprises a plastic tweezers main body and a removable metal weight.

The tweezers main body comprises a malleable material such as, for example, a plastic material. The main body is molded into a suitable shape to form the body of the dental tweezers.

The metal weight is inserted into the plastic tweezers main body and provides the disposable dental tweezers with a relative weight. This relative weight allows the dental tweezers of the present invention to feel similar to the conventional dental tool. As a result, dental professionals can easily replace the conventional dental tool with the disposable dental tweezers of the present invention without changing their technique.

Since the main body comprises an inexpensive material the cost of the dental tweezers is low and allows the main body of the dental tweezers to be disposed of after each use.

The dental tweezers of the present invention further comprises a use indicator for indicating that the dental tweezers has been previously used. When the use indicator encounters saliva or blood the use indicator will change color or dissolve. A patient can easily visually determine whether or not the dental tweezers has been previously used. As a result, contamination between patients is prevented.

The present invention further comprises a molded tweezers main body and a removable metal weight. The plastic tweezers main body comprises a hollow weight cavity. The metal weight is inserted into the hollow weight cavity. After the metal weight has been inserted base of the metal weight rests in a weight seat formed in the tweezers main body. After the dental tweezers have been used the weight is removed from the tweezers main body. The plastic tweezers main body is then disposed of and the metal weight is kept for future use. Since the metal weight is reusable the cost of the dental tweezers is reduced.

These and other objectives of the present invention will become obvious to those of ordinary skill in the art after reading the following detailed description of preferred embodiments.

It is to be understood that both the foregoing general description and the following detailed description are exemplary, and are intended to provide further explanation of the invention as claimed.

BRIEF DESCRIPTION OF THE DRAWINGS

The accompanying drawings are included to provide a further understanding of the invention, and are incorporated in and constitute a part of this specification. The drawings illustrate embodiments of the invention and, together with the description, serve to explain the principles of the invention. In the drawings.

DESCRIPTION OF THE PREFERRED EMBODIMENTS

Reference will now be made in detail to the preferred embodiments of the present invention, examples of which are illustrated in the accompanying drawings. Wherever possible, the same reference numbers are used in the drawings and the description to refer to the same or like parts.

Figure 1:
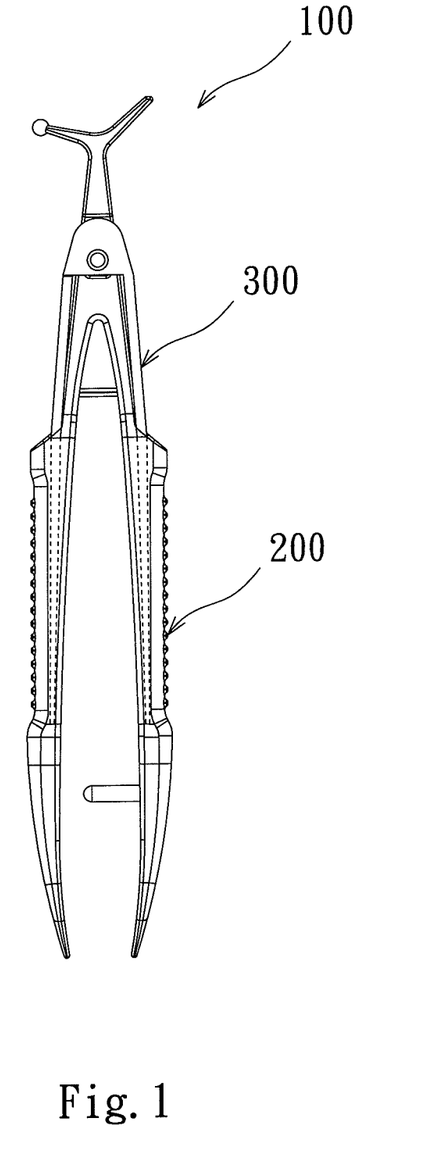
FIG. 1 is a drawing illustrating a disposable dental tweezers with removable metal weight according to an embodiment of the present invention.

Refer to FIG. 1, which is a drawing illustrating a disposable dental tweezers with removable metal weight according to an embodiment of the present invention.

The disposable dental tweezers with removable metal weight 100 comprises a plastic tweezers main body 200 and a metal weight 300.

The tweezers main body comprises a malleable material such as, for example, a plastic material. The main body is molded into a suitable shape to form the body of the dental tweezers.

The metal weight 300 is inserted into the plastic tweezers main body 200 and provides the disposable dental tweezers 100 with a relative weight. This relative weight allows the dental tweezers 100 of the present invention to feel similar to the conventional dental tool.

Figure 2:
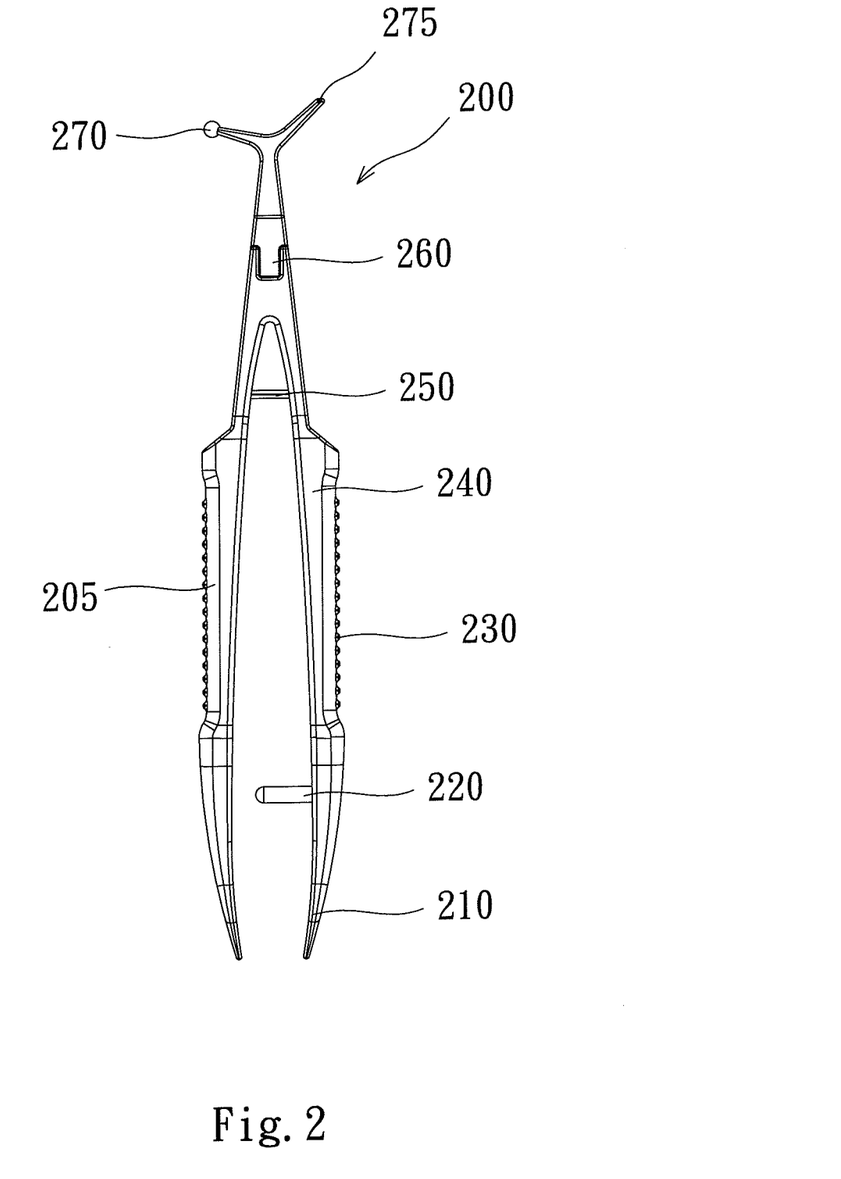
FIG. 2 is a front view drawing illustrating a plastic tweezers main body of a disposable dental tweezers according to an embodiment of the present invention.
Figure 3:
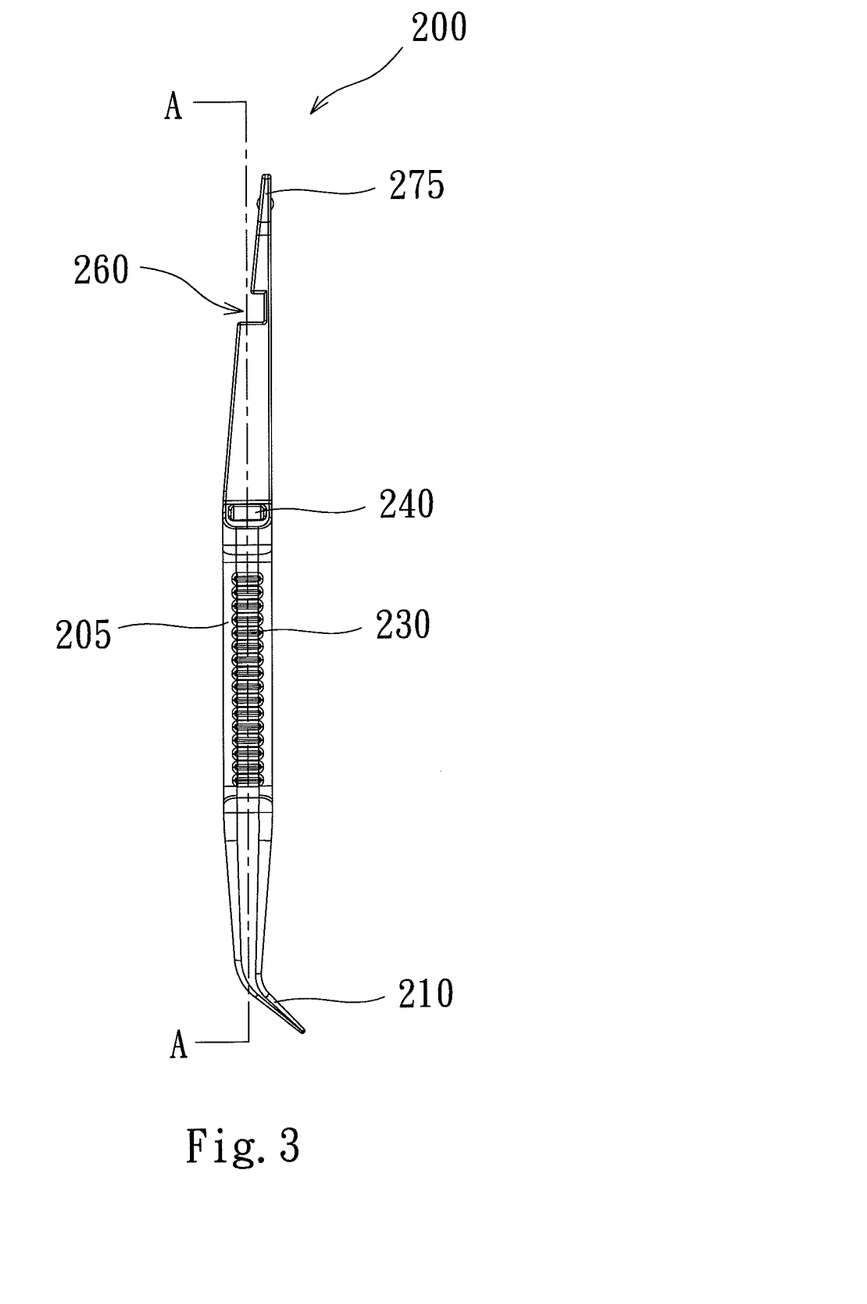
FIG. 3 is a side view drawing illustrating a plastic tweezers main body of a disposable dental tweezers according to an embodiment of the present invention.
Figure 4:
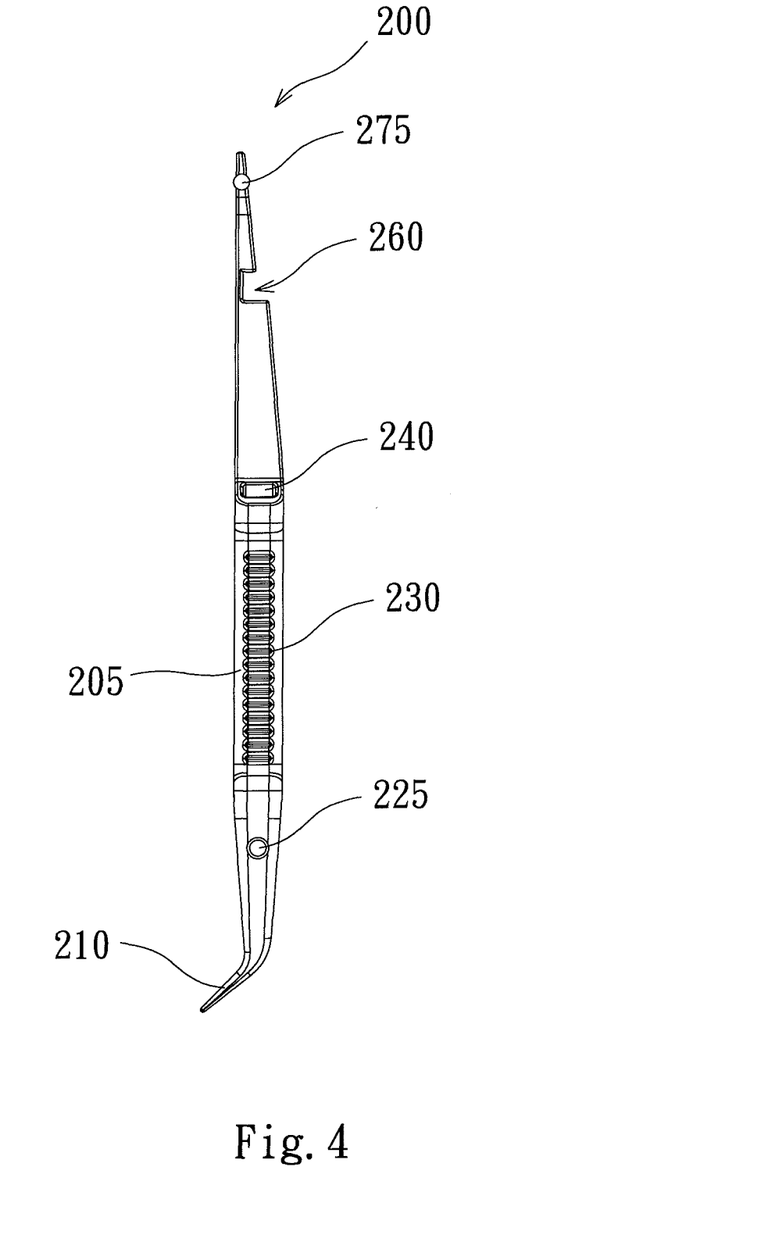
FIG. 4 is a side view drawing illustrating a plastic tweezers main body of a disposable dental tweezers according to an embodiment of the present invention.
Figure 5:
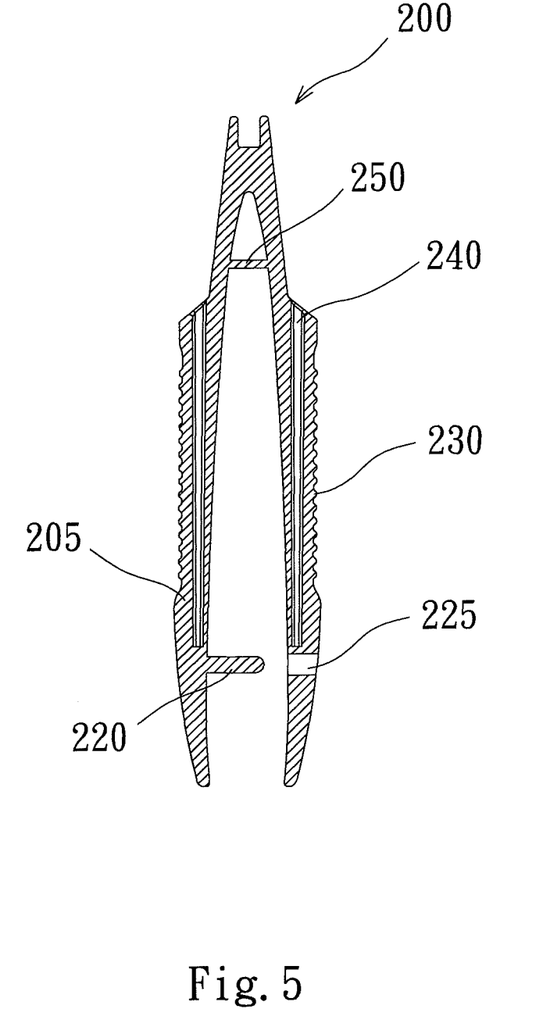
FIG. 5 is a cross-sectional view drawing illustrating a plastic tweezers main body of a disposable dental tweezers according to an embodiment of the present invention.

Refer to FIG. 2, which is a front view drawing illustrating a plastic tweezers main body of a disposable dental tweezers according to an embodiment of the present invention, to FIG. 3, which is a side view drawing illustrating a plastic tweezers main body of a disposable dental tweezers according to an embodiment of the present invention, to FIG. 4, which is a side view drawing illustrating a plastic tweezers main body of a disposable dental tweezers according to an embodiment of the present invention, and to FIG. 5, which is a cross-sectional view drawing illustrating a plastic tweezers main body of a disposable dental tweezers according to an embodiment of the present invention.

The dental tweezers main body 200 comprises tweezers arms 205, tweezers tips 210, a post 220, a post hole 225, a grip 230, a weight cavity 240, a bridge 250, a weight seat 260, a stir tip 270, and a utility tip 275.

The tweezers tips 210 are disposed on the ends of the tweezers arms 205. The flexibility of the tweezers arms 205 allow the tweezers arms 205 to be squeezed until the tweezers tips 210 touch each other. When the tweezers arms 205 are compressed or squeezed the tweezers tips 210 are able to grasp and hold an object or material between the two tweezers tips 210. The tweezers tips 210 of the tweezers arms 205 taper in diameter until the end of the tweezers tips 210.

A grip 230 is provided on the outside surface of the tweezers arms 205. The grip 230 comprises a plurality of ridges to improve the ability to grasp the dental tweezers.

The post 220 is disposed on the inside surface of one of the tweezers arms 205. The post hole 225 is disposed directly opposite the post 220 on the other tweezers arm 205. When the tweezers arms 205 are squeezed or compressed the post 220 enters the post hole 225. When the post 220 is inside the post hole 225 the tweezers arms 205 are prevented from twisting or bending. As a result, the tweezers tips 210 are kept in alignment and will be in the correct position when the tweezers tips 210 touch each other. Without the post 205 and the post hole 225 the tweezers arms 205 are susceptible to bending and the tweezers tips 210 will not touch each other at the very end of the tips.

The bridge 250 is disposed between the tweezers arms 205 close to where the tweezers arms 205 ends. The bridge 250 increases the tension between the tweezers arms 205 to improve resistance when squeezing the tweezers arms 205 together.

At the opposite end of the tweezers main body 200 from the tweezers tips 210 are the stir tip 270 and the utility tip 275. The stir tip 270 is used for mixing or stirring. The stir tip 270 is used for stirring when mixing dental products such as, for example, cement, paste, or filling material.

The utility tip 275 is a multipurpose tool. The utility tip 270 comprises, for example, a pick, a packer, or a trowel.

It should be noted that the stir tip 270 and the utility tip 275 do not interact or come into direct contact with a patient. The stir tip 270 and the utility tip 275 are used by the dental professional to complete tasks related to a dental procedure but are not used in a direct dental procedure in a patient's mouth.

The weight cavity 240 is a hollow chamber disposed inside both tweezers arms 205. The weight cavity 240 extends through the tweezers arms 205 and ends near the location of the post 220 and the post hole 225. The weight cavity 240 is provided for holding the removable metal weight.

The weight seat 260 is disposed between the end of the tweezers main body 200 where the stir tip 270 and utility tip 275 are located and where the tweezers arms 205 begin. The weight seat 260 if provided for holding the removable metal weight after the metal weight has been inserted into the weight cavity 240.

Figure 6:
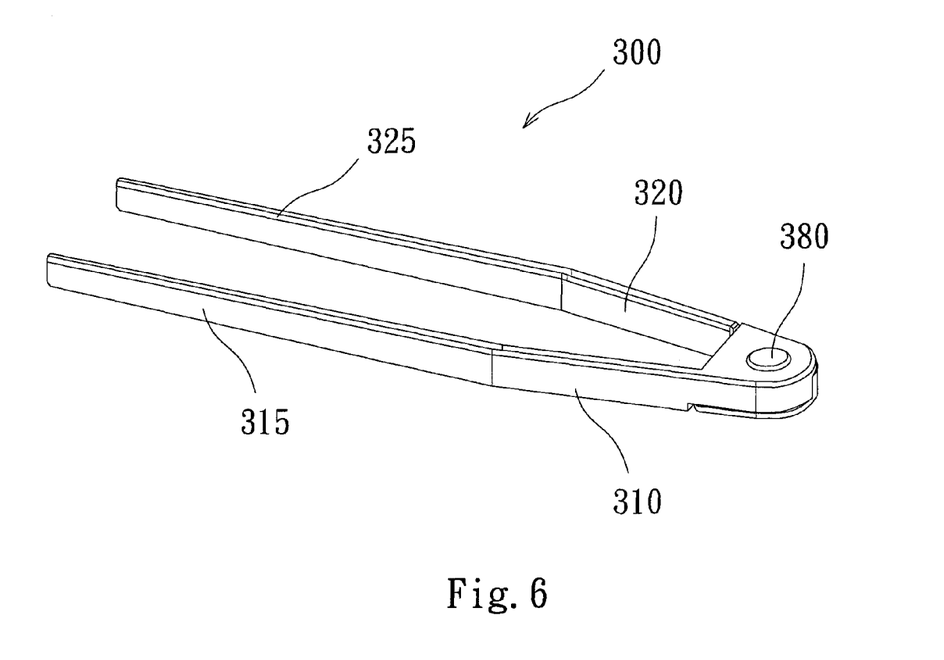
FIG. 6 is a drawing illustrating a metal weight of a disposable dental tweezers according to an embodiment of the present invention.
Figure 7:
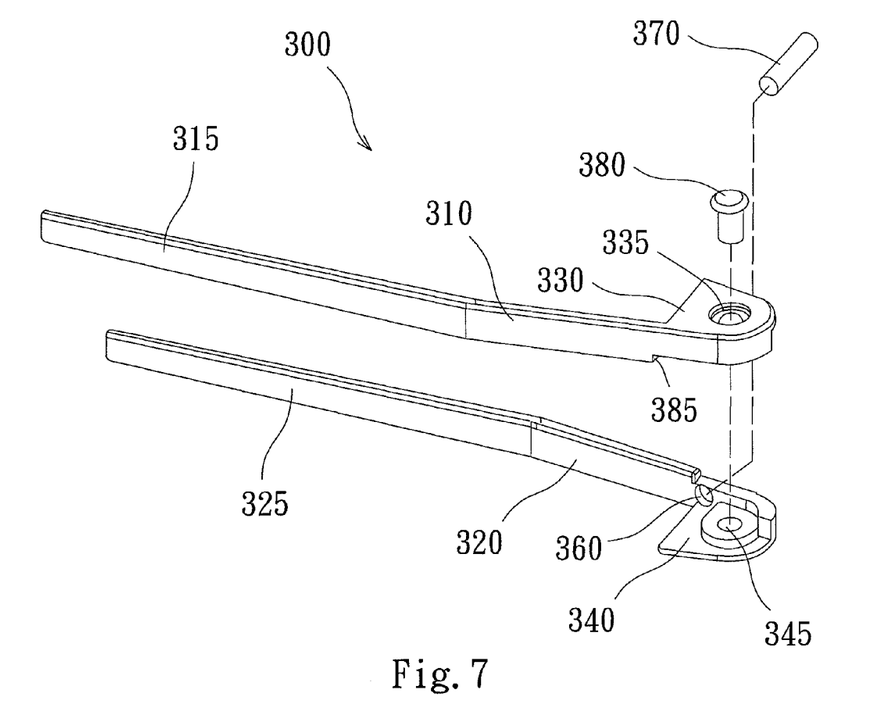
FIG. 7 is an exploded view drawing illustrating a metal weight of a disposable dental tweezers according to an embodiment of the present invention.

Refer to FIG. 6, which is a drawing illustrating a metal weight of a disposable dental tweezers according to an embodiment of the present invention, and to FIG. 7, which is an exploded view drawing illustrating a metal weight of a disposable dental tweezers according to an embodiment of the present invention.

The metal weight 300 is provided for adding weight to the plastic tweezers body. The metal weight 300 is inserted into the weight cavity of the tweezers main body and is held in the weight seat during use. After the dental tweezers have been used the metal weight 300 is removed from the plastic tweezers main body. The plastic tweezers main body is then disposed of and the metal weight 300 is retained for future use in a new and unused dental tweezers main body.

The metal weight 300 comprises a first weight 310, a first weight arm 315, a second weight 320, a second weight arm 325, a first base 330, a first pin hole 335, a second base 340, a second pin hole 345, a first flexible post seat (not shown), a second flexible post seat 360, a flexible post 370, and a pin 380.

The first weight 310 and the second weight 320 are the same shape and have the same features. For example, the first weight 310 and the second weight 320 are produced by the same tooling design and are the same pieces. By flipping one of the weights over the weights are complements each other. This is a cost savings benefit of the present invention as tooling costs are reduced and inventory is easier to manage.

The first weight 310 comprises a first weight arm 315, a first base 330, a first pin hole 335, a first flexible post seat (not shown), and a first base indent 385.

The first weight arm 315 is the section of the first weight 310 that is inserted into the weight cavity of the plastic tweezers main body. The first pin hole 335 is formed in the first base 330. An angled section of the first weight 310 connects the first weight arm 315 and the first base 330. The angled section of the first weight 310 conforms to the shape of the tweezers main body.

The second weight 320 comprises a second weight arm 325, a second base 340, a second pin hole 345, a second flexible post seat 360, and a second base indent.

Similar to the first weight 310, the second weight arm 325 is the section of the second weight 320 that is inserted into the weight cavity of the plastic tweezers main body. The second pin hole 345 is formed in the second base 330. An angled section of the second weight 320 connects the second weight arm 325 and the second base 340. The angled section of the second weight 320 conforms to the shape of the tweezers main body.

The flexible post 370 comprises a flexible material that can be compressed. The flexible material comprises, for example, a rubber material, a composite rubber material, or a synthetic flexible material. The flexible post 370 acts like a spring to provide resistance to compression.

The pin 380 is a fastener for connecting the first weight 310 and the second weight 320 together. The pin 380 comprises, for example, a pin, a rivet, a spreadable fastener, a self-taping screw, or other type of fastener capable of holding the two weights together.

To assemble the removable metal weight 300 the flexible post 370 is inserted into the indentation of the second flexible post seat 360 of the second weight 320. The first weight 310 is positioned so that the first base 330 and the second base 340 make contact with each other and the other end of the flexible post 370 is inserted into the indentation of the first flexible post seat of the first weight 310. A first base indent 385 of the first base 330 of the first weight 310 mates with the second base 340 of the second weight 320. Once the first weight 310 and the second weight 320 have been correctly positioned with the flexible post 370 inside the first base 330 and the second base 340, the pin 380 is inserted into the first pin hole 335 and the second pin hole 345 and holds the metal weight 300 assembly together.

Refer to FIGS. 1-7 in conjunction with the following description of the assembly process and the disassembly process.

After the metal weight 300 has been assembled as shown in FIG. 6 and the plastic tweezers main body 200 has been produced using a molding process, the disposable dental tweezers 100 is ready for assembly.

The first weight arm 315 is inserted into the opening of one of the weight cavities 240 at the same time the second weight arm 325 is inserted into the opening of the other weight cavity 240.

The metal weight 300 is pushed forward and the first weight arm 315 and the second weight arm 325 continue penetrating the weight cavity 240 deeper. The combined first base 330 and second base 340 slides along the end of the tweezers main body near the stir tip 270 and the utility tip 275 until they reach the weight seat 260. When the combined first base 330 and second base 340 reach the weight seat 260 they will snap into and be held by the weight seat 260. At this point the metal weight 300 is now held in the plastic tweezers main body 200 and assembly of the disposable dental tweezers 100 is complete.

After the disposable dental tweezers 100 have been used the dental tweezers 100 can be disassembled. By grasping the combined first base 330 and second base 340 and pulling them away from the tweezers main body 200, the combined first base 330 and second base 340 are ejected from the weight seat 260. The metal weight 300 is then pulled back and the first weight arm 315 and the second weight arm 325 exit the weight cavities 240. When the metal weight 300 and the plastic tweezers main body 200 are separated the plastic tweezers main body 200 is disposed of in a proper manner and will not be used again. The metal weight 300 is kept for future use in a new unused plastic tweezers main body 200. When the metal weight 300 is used again in a new plastic tweezers main body 200 the assembly process described above is performed.

Since the metal weight 300 has not come into direct contact with a patient, the patient's saliva, or the patient's blood, the metal weight 300 is free of contamination and can be safely used again. Being able to re-use the metal weight 300 provides a cost savings benefit.

Also, since the plastic tweezers main body 200 comprises an inexpensive plastic material the cost of the dental tweezers is low.

Figure 8:
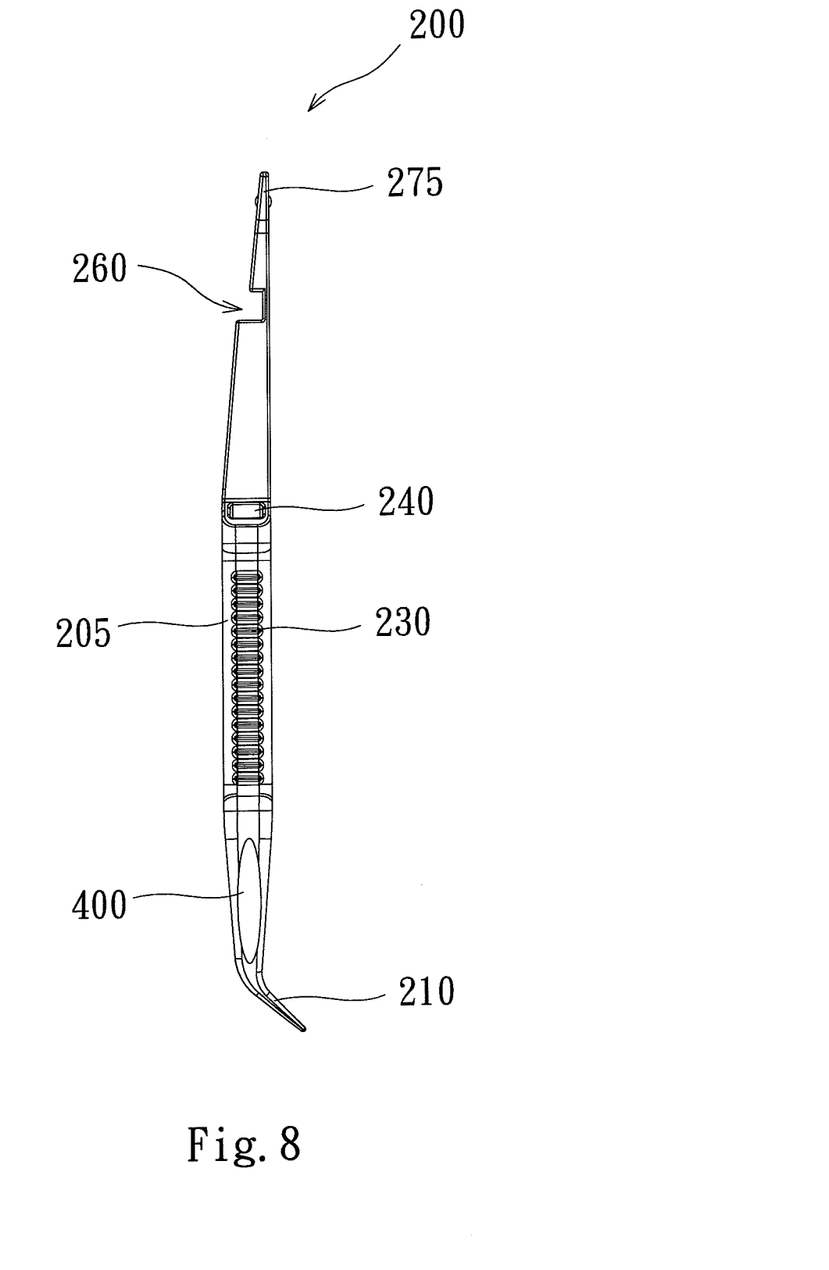
FIG. 8 is a drawing illustrating a plastic tweezers main body with use indicator of a disposable dental tweezers according to an embodiment of the present invention.

Refer to FIG. 8, which is a drawing illustrating a plastic tweezers main body with use indicator of a disposable dental tweezers according to an embodiment of the present invention.

In an embodiment of the present invention the plastic tweezers main body 200 further comprises a use indicator 400 for indicating that the dental tweezers main body 200 has been previously used. When the use indicator 400 encounters saliva or blood the use indicator 400 will change color or dissolve. A patient can easily visually determine whether or not the tweezers main body 200 has been previously used. As a result, contamination between patients is prevented.

When the tips 210 of the dental tweezers arms 205 enters a patient's mouth the use indicator 400 makes contact with the patient's gums, teeth, lips, cheeks, tongue, or other parts of the mouth, or saliva, blood, or plaque. The properties or characteristics of the material used in the use indicator 400 will cause the use indicator 400 to change visually. For example, if the use indicator 400 is originally white and once the use indicator 400 enters a patient's mouth and makes contact with an area of the mouth, saliva in the mouth, blood in the mouth, or plaque, the use indicator 400 will change color.

The material used in manufacturing the use indicator 400 comprises a material or chemical compound with characteristics or properties that allow the material or chemical compound to change properties when encountering saliva, blood, or plaque.

For example, a litmus material or mixture is used in an adhesive tape and adhered to the tweezers main body 200 of the dental tweezers near the tips 210. When the water-soluble litmus mixture contacts saliva the color of the use indicator 400 will change.

Or, for example, an easily dissolve-able material is used as the use indicator 400. When the use indicator 400 encounters moisture such as blood or saliva the material will start to dissolve. A patient or professional can easy see the deterioration of the use indicator 400 and identify that the dental tweezers main body 200 has been previously used.

Or. For example, an absorbent material is used as the use indicator 400. When the use indicator 400 encounters blood, the blood is absorbed into the use indicator 400 and a portion of the use indicator 400 turns red from the blood stain.

In some embodiments of the present invention the use indicator 400 extends over part or the entire exposed portion of the tips 210. In this way, when the tips 210 make contact inside the patient's mouth the use indicator 400 will visually indicate that the dental tweezers main body 200 has been used.

As soon as the use indicator 400 encounters saliva, blood, or other fluid the use indicator 400 will indicate the main tweezers body 200 has been used. The use indicator 400 will make an indication the very first time the dental main body 200 is used.

In an embodiment of the present invention one use indicator 400 is disposed on an outer side of one tweezers arm 205 and/or tweezers tips 210.

In another embodiment of the present invention a use indicator 400 is disposed on both tweezers arms 205 and/or tweezers tips 210.

It will be apparent to those skilled in the art that various modifications and variations can be made to the present invention without departing from the scope or spirit of the invention. In view of the foregoing, it is intended that the present invention cover modifications and variations of this invention provided they fall within the scope of the invention and its equivalent.

What is claimed is:

1. A dental tweezers comprising:
a plastic tweezers main body, the plastic tweezers main body comprising:
a pair of tweezers arms, the tweezers arms comprising:
a pair of tweezers tips disposed on the pair of tweezers arms;
a pair of weight cavities disposed in the pair of tweezers arms; and
a grip disposed on an outer surface of the pair of tweezers arms; and
a removable metal weight attached to the plastic tweezers main body, the removable metal weight extending into the pair of weight cavities.

2. The dental tweezers of claim 1, the removable metal weight comprising:
a first base;
a first weight arm extending from the first base;
a first pin hole disposed in the first base; and
a first base indent in the first base;
a second weight, the second weight comprising:
a second base;
a second weight arm extending from the second base;
a second pin hole disposed in the second base; and
a second base indent in the second base; and
a flexible post disposed between the first base indent and the second base indent; and
a pin positioned in the first pin hole and the second pin hole for holding the first weight and the second weight together.

3. The dental tweezers of claim 1, the plastic tweezers main body further comprising:
a bridge disposed between the pair of tweezers arms.

4. The dental tweezers of claim 1, the plastic tweezers main body further comprising:
a stir tip disposed on an opposite end of the plastic tweezers main body from the pair of tweezers tips.

5. The dental tweezers of claim 1, the plastic tweezers main body further comprising:
a weight seat for holding the removable metal weight to the plastic tweezers main body.

6. The dental tweezers of claim 1, the plastic tweezers main body further comprising:
a post disposed on an inside surface of one of the pair of tweezers arms; and
a post hole disposed on one of the pair of tweezers arms opposite the post.

7. The dental tweezers of claim 1, the plastic tweezers main body further comprising:
a use indicator disposed on the pair of tweezers arms for indicating that the plastic tweezers main body has been used.

8. The dental tweezers of claim 7, the use indicator comprising a water-soluble material or mixture that changes color on first contact with saliva or blood.

9. The dental tweezers of claim 1, wherein after the dental tweezers have been used the removable metal weight is separated from the plastic tweezers main body, the plastic tweezers main body is disposed of, and the removable metal weight is retained for future use with an unused plastic tweezers main body.

10. A dental tweezers comprising:
a plastic tweezers main body, the plastic tweezers main body comprising:
a pair of tweezers arms, the tweezers arms comprising:
a pair of tweezers tips disposed on the pair of tweezers arms;
a pair of weight cavities disposed in the pair of tweezers arms;
a grip disposed on an outer surface of the pair of tweezers arms; and
a weight seat; and
a removable metal weight held in place on the plastic tweezers main body by the weight seat, the removable metal weight extending into the pair of weight cavities.

11. The dental tweezers of claim 10, the removable metal weight comprising:
a first base;
a first weight arm extending from the first base;
a first pin hole disposed in the first base; and
a first base indent in the first base;
a second weight, the second weight comprising:
a second base;
a second weight arm extending from the second base;
a second pin hole disposed in the second base; and
a second base indent in the second base; and
a flexible post disposed between the first base indent and the second base indent; and
a pin positioned in the first pin hole and the second pin hole for holding the first weight and the second weight together.

12. The dental tweezers of claim 10, the plastic tweezers main body further comprising:
a bridge disposed between the pair of tweezers arms.

13. The dental tweezers of claim 10, the plastic tweezers main body further comprising:
a stir tip disposed on an opposite end of the plastic tweezers main body from the pair of tweezers tips.

14. The dental tweezers of claim 10, the plastic tweezers main body further comprising:
a post disposed on an inside surface of one of the pair of tweezers arms; and
a post hole disposed on one of the pair of tweezers arms opposite the post.

15. The dental tweezers of claim 10, the plastic tweezers main body further comprising:
a use indicator disposed on the pair of tweezers arms for indicating that the plastic tweezers main body has been used.

16. The dental tweezers of claim 15, the use indicator comprising a water-soluble material or mixture that changes color on first contact with saliva or blood.

17. The dental tweezers of claim 10, wherein after the dental tweezers have been used the removable metal weight is separated from the plastic tweezers main body, the plastic tweezers main body is disposed of, and the removable metal weight is retained for future use with an unused plastic tweezers main body.

18. A dental tweezers comprising:
a plastic tweezers main body, the plastic tweezers main body comprising:
a pair of tweezers arms, each tweezers arm comprising:
a tweezers tip disposed on an end of the tweezers arm;
a weight cavity disposed in the tweezers arm; and
a grip disposed on an outer surface of the tweezers arm;
a bridge disposed between the pair of tweezers arms;
a stir tip disposed on an opposite end of the plastic tweezers main body from the tweezers tips;
a weight seat disposed between the stir tip and the bridge;
a post disposed on an inside surface of one of the pair of tweezers arms;

a post hole disposed on the tweezers arm opposite the post; and
a use indicator disposed on the pair of tweezers arms for indicating that the plastic tweezers main body has been used; and
a removable metal weight held in place on the plastic tweezers main body by the weight seat, the removable metal weight comprising:
a first weight, the first weight comprising:
a first base;
a first weight arm extending from the first base and into one of the pair of weight cavities;
a first pin hole disposed in the first base; and
a first base indent in the first base;
a second weight, the second weight comprising:
a second base;
a second weight arm extending from the second base and into another one of the pair of weight cavities;
a second pin hole disposed in the second base; and
a second base indent in the second base; and
a flexible post disposed between the first base indent and the second base indent; and
a pin positioned in the first pin hole and the second pin hole for holding the first weight and the second weight together;
wherein after the dental tweezers have been used the removable metal weight is separated from the plastic tweezers main body, the plastic tweezers main body is disposed of, and the removable metal weight is retained for future use with an unused plastic tweezers main body.

19. The dental tweezers of claim 18, the use indicator comprising a water-soluble material or mixture that changes color on first contact with saliva or blood.

20. The dental tweezers of claim 18, wherein after the dental tweezers have been used the removable metal weight is separated from the plastic tweezers main body, the plastic tweezers main body is disposed of, and the removable metal weight is retained for future use with an unused plastic tweezers main body.

* * * * *